United States Patent [19]

Polak et al.

[11] Patent Number: 5,409,903
[45] Date of Patent: Apr. 25, 1995

[54] METHOD AND COMPOSITIONS FOR THE TREATMENT OF *H. PYLORI* AND DERMATITIS

[75] Inventors: Robert B. Polak; Attallah Kappas, both of New York, N.Y.

[73] Assignee: Urecap Corporation, New York, N.Y.

[21] Appl. No.: 837,332

[22] Filed: Feb. 18, 1992

[51] Int. Cl.⁶ .................. A61K 9/50; A61K 15/00; A61K 9/26
[52] U.S. Cl. .................................. 514/23; 424/402; 424/447; 424/449; 424/451; 424/464; 424/489; 424/499; 514/865; 514/870; 514/925; 602/904
[58] Field of Search ............... 514/925, 23, 870, 865; 128/360; 602/904; 424/402, 447, 449, 451, 464, 489, 499

[56]  References Cited

U.S. PATENT DOCUMENTS

| | | | |
|---|---|---|---|
| 3,679,792 | 7/1972 | Litchfield et al. | 424/48 |
| 3,823,233 | 7/1974 | Giordano et al. | 514/870 |
| 4,034,084 | 7/1977 | Siragusa | 514/60 |
| 4,382,919 | 5/1983 | Alonso et al. | 424/47 |
| 4,460,555 | 7/1984 | Thompson | 210/638 |
| 4,569,946 | 2/1986 | LeVeen | 514/693 |
| 4,582,705 | 4/1986 | Primes et al. | 514/474 |
| 4,585,797 | 4/1986 | Cioca | 514/773 |
| 4,590,214 | 5/1986 | Zamore | 514/928 |
| 4,650,587 | 3/1987 | Polak et al. | 210/638 |
| 4,670,256 | 6/1987 | Doran | 424/DIG. 14 |
| 4,842,863 | 6/1989 | Nishimura et al. | 424/498 |
| 4,856,509 | 8/1989 | Lemelson | 128/206.19 |
| 4,900,552 | 2/1990 | Sanvordeker et al. | 424/422 |
| 4,923,801 | 5/1990 | Marshall et al. | 435/12 |
| 4,940,695 | 7/1990 | Coveney et al. | 514/925 |
| 4,963,431 | 10/1990 | Goldstein et al. | 428/360 |
| 4,977,892 | 12/1990 | Ewall | 523/105 |
| 4,990,339 | 2/1991 | Scholl et al. | 523/105 |
| 5,008,114 | 4/1991 | Lourecich | 424/484 |
| 5,021,597 | 6/1991 | Fodor et al. | 514/927 |
| 5,039,699 | 8/1991 | Kurihara et al. | 514/925 |
| 5,047,244 | 9/1991 | Sanvordeker et al. | 424/435 |
| 5,081,157 | 1/1992 | Pomerantz | 514/925 |
| 5,103,812 | 4/1992 | Salamone et al. | 424/447 |
| 5,154,919 | 10/1992 | Des Garets | 523/105 |

FOREIGN PATENT DOCUMENTS

| | | |
|---|---|---|
| WO84/00885 | 3/1984 | European Pat. Off. |
| 0224856 | 6/1987 | European Pat. Off. |
| 0341951 | 11/1989 | European Pat. Off. |

OTHER PUBLICATIONS

Chem. Abstract 103:129004d, p. 356 (1985) Shimizu, T., et al.
Chem. Abstract 99:93694m, p. 348 (1983) Shimizu, T., et al.
Chem. Abstract 102:32213m, p. 483 (1985), Shimizu, T., et al.
Chem. Abstract 107:161632a, p. 479 (1987) Chen, Y., et al.

(List continued on next page.)

*Primary Examiner*—Ronald W. Griffin
*Attorney, Agent, or Firm*—Klauber & Jackson

[57]  ABSTRACT

A method of treating a mammal for the presence or the activity of *H. pylori* in the gastrointestinal tract is disclosed. The method encompasses orally administering to said mammal a sufficient amount of a scavenging, reacting or inactivating compound to remove bicarbonate ions, ammonium ions or urea which are present in combination with the microorganisms which colonize and infect the gastric mucosa. Such microorganisms have been implicated in gastritis, gastric ulcer disease and as a risk factor in gastric carcinoma.

Also, the invention encompasses a method, utilizing similar compounds, for the treatment or prevention of dermatitis such as diaper rash wherein these compounds are preapplied to the skin or used to treat the diaper prior to use.

Also included are compositions which are used for the methods described above.

35 Claims, No Drawings

OTHER PUBLICATIONS

Chem. Abstract 110:51292t, p. 73 (1989) Yu, J., et al.
Chem. Abstract 107:176363m, (1987) Ghosh, P., et al.
Chem. Abstract 109:191146d, (1988) Shimokawa, W., et al.
Chem. Abstract 106:140435c, p. 122 (1987) Shimizu, T., et al.
Chem. Abstract 104:174599h, p. 387 (1986) Shimizu, T., et al.
Chem. Abstract 104:102212d, p. 47 (1986) Nakabayashi, N., et al.
Abstract No. 1636505 85161505 Koshikawa, S. "Oral Medication to Supplement Kidney Function" *Kango Gijutsu* (Feb. 1985) 31(3) pp. 373–374.
Thompkins, D. S. "Campylobacter pylori, acid, and bile" *J. Clin. Pathol.* 40:1387 (1987).
Leyden, J., et al. "Urinary Ammonia and Ammonia--Producing Microorganisms in Infants With and Without Diaper Dermatitis", *Arch. Dermatol.* 113:1678–1680 (1977).
Shalaby, W., et al. "In vitro and in vivo studies of enzyme-digestible hydrogels for oral drug delivery", *J. Cont. Release* 00:1–14 (1991).
"Dialysis on the Move", *Breakthrough* by Boardroom Reports vol. IV (9) pp. 2–3 (1986).
*Bioadhesive Drug Delivery Systems*, Lenaerts, V., et al. (eds) CRC Press, Inc. Chapter 5 (pp. 94–104 ), 7 (pp. 137–151) and 10 (pp. 179, 189–193) (1990).
*Pediatrics* 17 ed. Rudolph, A. M., et al. (eds) (p. 855). (1982).
*Pediatric Dermatology* 3 (2) p. 104 (Feb. 1986).
*Pediatric Dermatology* Schachner, L. A., et al. (eds.) vol. 1, pp. 708–710 (1988).
Blaser, M. J. "Helicobacter Pylori", *Prin. Pract. Infec. Dis.* Update 9 pp. 3–10 (1991).
UOP *Molecular Sieves* product brochure (1990).
Linde Molecular Sieves, "Ion Exchange Separations with Molecular Sieve Zeolites" *Ion Exchange Bulletin* Product Brochure (1977).
Onishi, Hiraku and Tsuneji, Nagai, "Characterization and evaluation of dialdehyde starch as an erodible medical polymer and a drug carrier", International Journeal of Pharmaceutics, vol. 30, pp. 133–141 (1986).
Ash, S. R. et al., "In vivo Evaluation of Calcium Loaded Zeolites and Urease for Urea Removal in Hemodialysis", Trans. Am. Soc. Artif. Intern. Organs, vol. XXVI, pp. 111–115 (1980).

METHOD AND COMPOSITIONS FOR THE TREATMENT OF H. PYLORI AND DERMATITIS

The invention described herein relates to a method and composition for the treatment of the presence or activity of urease containing bacteria which are implicated in various ailments. One such bacteria, *Helicobacter pylori* ("*H. pylori*") has been implicated as a causative agent in several gastrointestinal disorders. In another case, the invention described herein encompasses the amelioration, treatment or prevention of skin rash or dermatitis wherein urease containing bacteria, bacterial components and by-products thereof are implicated in causing such conditions.

BACKGROUND OF THE INVENTION

Microbial ureases are important enzymes in certain human and animal pathogenic states, in ruminant metabolism and in environmental transformation of certain nitrogenous compounds.

Bacterial urease is implicated in the pathogenesis of many clinical conditions. It is directly associated with the formation of infection stones and contributes to the pathogenesis of pyelonephritis, ammonia encephalopathy, hepatic coma, urinary catheter encrustation and peptic ulceration. Bacterial urease in feces also plays a prominent role in diaper dermatitis (also known as diaper rash). This invention attempts to ameliorate two of these conditions, namely; gastrointestinal diseases associated with *H. pylori* and diaper dermatitis.

*H. pylori* is presently being studied and has been implicated in several gastrointestinal diseases. Formerly known as *Campylobacter pylori* or Pylordis, this organism was first isolated from humans in 1982. *The Principals and Practice of Infectious Diseases*, Update No. 9 (1991) pages 1–10 contains a cumulative description of the characteristics *H. pylori* and its association with gastrointestinal disease. In particular, these organisms have been implicated in chronic diffuse and Type A gastritis as well as gastric and duodenal ulcers.

Since *H. pylori* is closely associated with chronic gastritis, which in turn is a well-known risk factor for the development of gastric carcinoma, it has been postulated that there is a role for this organism in the development of such carcinomas. A number of recently published studies appears to further confirm that *H. pylori* is a risk factor in the development of gastric cancer. (Parsonnet, et al. *New Eng. J. Med.*, Oct. 1991: 1127–1131; Nomura, et al., *New Eng. J. Med.*, Oct. 1991: 1132–1136).

The organism has been isolated from the gastric environment, which is generally hostile to bacterial growth, and it has further been postulated that the organism colonizes the gastric mucosa and generates a protective layer or sheath which contains ammonia, which shields the microorganism from acid inactivation. While it has not been mentioned in the literature, we believe that bicarbonate ions also offer a measure of protection to the organism in this environment.

At present there is no fully accepted therapy for the eradication of *H. pylori*. The most widely used approach in research studies is a combination therapy employing a bismuth salt and one or two antibiotics such as metronidazole, amoxicillin or tetracycline. These therapies are not fully successful, and run the risk of adverse effects such as medication-induced upper GI symptoms, antibiotic-associated colitis and candidiasis. Therefore, one objective of the present invention is to provide a new and superior method to minimize or eradicate the presence or activity of *H. pylori* in the gastrointestinal tract. As such, it is believed that treatment and eradication of *H. pylori* reduces the incidence or severity of gastritis and ulcer disease and as a result may also remove a causative factor for the development of gastric carcinoma.

The present invention also relates to the treatment of skin rash or dermatitis caused or aggravated by urease containing bacterial organisms, components of such organisms and compounds produced by such organisms.

Few infants or incontinent adults escape several episodes of such irritant induced contact dermatitis, which is generally known as diaper rash or diaper dermatitis. This is a common occurrence since the diapered skin is frequently exposed to a warm, moist environment and increases in the hydration of the skin, which cause increased friction, abrasion and permeability. In addition, under these circumstances the microbial count also rises.

For many years the prevailing explanation for the development of diaper rash involved the bacterial decomposition of urine with the formation of ammonia, which was considered to be the primary irritant. The work of Layden et al. *Arch Dermatol.* 113:1678–1680 (1977), however, suggested that ammonia per se was not a primary factor in the induction of this condition.

As a result of recent experimental work, an indirect role has been assigned for the ammonia resulting from the interaction of the fecal urease containing bacteria and urine. In this model, the direct irritation effect on the skin can be attributed to fecal enzymes, particularly proteases and lipases. These enzymes become more active and thus more damaging as the pH increases. The increase in pH is the result of ammonia production from urinary urea through the action of fecal urease. Also, while not generally acknowledged in the literature, the bicarbonate ions generated as a result of urea hydrolysis, also tend to increase the pH.

Since urine and feces are commonly present in the diaper at the same time, and exposure to the skin for several hours is not uncommon, suitable conditions and ample time are available for this interaction and the resulting skin damage to occur.

This type of dermatitis can range in severity from mild erythema to severely inflamed tissue with secondary bacterial infection.

The most common treatment for diaper rash is directed toward cleaning and drying the involved area. According to this regime, the soiled diaper should be changed as soon as possible and talcum powder, corn starch or another such product is applied to the affected area.

Since the enzymes which actually cause skin irritation are believed to be potentiated by ammonia and bicarbonate, reducing the presence or activity of these compounds and/or the urea substrate should reduce the incidence of diaper dermatitis. Further, keeping the enzymes away from the skin should also lead to a positive outcome. Consequently, another object of the present invention is to provide a composition which reduces the incidence or severity of such dermatitis.

SUMMARY OF THE INVENTION

A method of treating a mammal for the presence or activity of *H. pylori* in the gastrointestinal tract is disclosed, wherein such *H. pylori* is in the presence of bicarbonate ions, ammonium ions or urea. The method comprises orally administering to said mammal a sufficient amount of a scavenging, reacting or inactivating compound to remove said bicarbonate ions, ammonium ions or urea, thus permitting the bacteria to be inactivated by the acid environment of the stomach.

Additionally, a pharmaceutical composition is disclosed which is comprised of at least one compound selected from the group consisting of dibasic magnesium phosphate, dialdehyde polysaccharide, calcium acetate, calcium chloride, calcium gluconate, calcium lactate, magnesium chloride, magnesium citrate and zeolite.

The invention herein further encompasses a method of treating or preventing skin rash or dermatitis in a mammal caused by bacteria, a bacterial component, urea and/or ammonia, wherein the skin is exposed to a compound which scavenges, reacts with or deactivates the substrate used by or the products made by said bacteria. This in turn precludes a rise in pH which would otherwise permit an increase in the activity of the bacterial enzymes present.

Additionally, the invention described herein encompasses a composition for the treatment or prevention of skin rash or dermatitis which is comprised of at least one compound selected from the group consisting of dibasic magnesium phosphate, dialdehyde polysaccharide and zeolite. The activity of these compounds may be enhanced by adding at least one of the components selected from the group consisting of calcium acetate, calcium chloride, calcium gluconate, calcium lactate, magnesium chloride and magnesium citrate. The compounds are present in the composition in an amount effective for the inactivation or elimination of the substrate or end products produced by the bacteria or bacterial components, as well as for the treatment or prevention of skin rash, and are typically present in combination with a pharmaceutically acceptable carrier for such compounds which may separate the skin from the damaging enzymes and particulate matter.

DETAILED DESCRIPTION

The invention described herein utilizes at least one of a number of compounds which is useful in treating *H. pylori*, present in the stomach mucosal lining, thus rendering said microorganisms susceptible to the acid environment of the stomach. The compounds work via any number of different mechanisms which include reaction with bicarbonate ions, reaction with ammonium ions and urea, which facilitate the inactivation of said bacteria. As such, the materials may act as scavenging, reacting or inactivating compounds.

A preferred compound for use in the treatment of the gastrointestinal tract for the presence of *H. pylori* is a dibasic magnesium compound, such as dibasic magnesium phosphate. A preferred form of this compound is described in U.S. Pat. No. 4,650,587 (Polak et al.) and may be produced in accordance with the method outlined in U.S. Pat. No. 4,460,555 (Thompson) both incorporated herein by reference. Dibasic magnesium phosphate reacts with ammonium ions to form magnesium ammonium phosphate with a release of protons. Thus, in essence, this compound reacts with and removes the ammonia "cloud" surrounding *H. pylori* in the stomach mucosal lining.

A representative dose of dibasic magnesium phosphate for use in treating a mammal for the presence or activity of *H. pylori* in the gastrointestinal tract ranges from about 100 mgs to as high as about 3.0 g. Such doses may be repeated as often as appropriate.

A second compound which is particularly useful for treating a mammal for the presence or activity of *H. pylori* in the gastrointestinal tract is a dialdehyde polysaccharide, and most preferably a dialdehyde starch. Also known as oxystarch, polymeric dialdehyde, or oxidized starch, these components have previously been tested as chemisorbents in artificial kidney systems. Such use is conducted externally of the body at essentially mild acid to neutral pH. Similarly, surface treated oxystarch has been used to remove uremic waste metabolites from uremic blood and gastrointestinal juice. Approximately 0.2–1.0 g. is used in an in vitro absorption test, wherein the oxystarch surface is pretreated with albumin or gelatin. In these cases, uremic blood and gastrointestinal fluid have been treated to absorb urea.

The dialdehyde polysaccharide used in the present invention typically is oxidized at carbon atoms 2 and 3 of the monomeric subunits, thus producing 2 formyl groups per monomeric unit. Typically, the polymer contains at least about 20 monomeric units per molecule, and at least about 15% of the hydroxyl groups contained in the polymer are oxidized to form formyl groups. Most preferably, at least about 35 to 100% of the $C_2$ and $C_3$ hydroxyl groups are oxidized.

Doses of the dialdehyde polysaccharide composition which are effective for treating or eliminating the presence of *H. pylori* in the gastrointestinal tract range from about 100 mgs to as high as 3.0 g., which may be repeated as often as appropriate. It is believed that the dialdehyde polysaccharide reacts with urea and/or ammonia, or more particularly with ammonium ions, thus removing the protective basic environment which surrounds the microorganisms and permitting deactivation thereof by the acid environment of the stomach.

An alternative approach utilizes a chemical compound which reacts with bicarbonate ions to form an insoluble compound, and in this fashion removes the bicarbonate from solution. In this manner, a portion of the pH protection is removed from the organism.

To this end, an alternative preferred group of compounds for use in the invention described herein is a series of calcium salts. These salts include but are not limited to, calcium acetate, calcium chloride, calcium gluconate and calcium lactate. The calcium compounds useful herein are somewhat more soluble in aqueous media than the resultant product, and are believed to function as bicarbonate scavengers. It is believed that the these calcium compounds react with bicarbonate ions which are present in the protective base environment which surrounds *H. pylori* in the mucosal lining. As such, removal of the bicarbonate ions by reaction with calcium compounds tends to reduce the presence of the basic protective sheath and permit the acid environment to deactivate the microorganisms.

Doses of the various calcium compounds range from about 100 mg to as high as about 3.0 g., and such doses may be repeated as often as appropriate.

Another preferred group of compounds for use herein is drawn to particular magnesium compounds, including but not limited to magnesium chloride and magnesium citrate. These compounds are also believed to react with bicarbonate as described above with respect to the soluble calcium compounds, to form progressively more insoluble magnesium carbonate which may further react to form magnesium hydroxide. As such, the magnesium compounds remove the bicarbonate present in the basic pH sheath surrounding the *H. pylori* in the gastric mucosa.

Doses of the soluble magnesium compounds range from about 100 mgs to as high as about 3.0 g, and such dosages may be repeated as appropriate.

Another preferred compound for use in the invention described herein are zeolite molecular sieves. Zeolites are crystalline aluminosilicates, most commonly, of sodium, potassium, magnesium, calcium, barium and strontium ions. The aluminosilicate portion of the structure is a three-dimensional open frame work.

The preferred zeolites for use herein act as ion exchange compositions, absorbing ammonium ions and releasing cations, e.g., sodium, calcium or potassium, depending upon the cations which are incorporated in the particular zeolite composition. The ion exchange capacity and selectivity of such zeolite ion exchangers is a function of the $SiO_2/Al_2O_3$ mole ratio, the cations contained in the compound and the pore sizes in the structure. The zeolites with the highest ion exchange capacity and selectivity will be the most preferable for the application. One such zeolite is UOP Molecular Sieve Type IE-W-85, which is available as a mixed sodium/potassium powder. Doses of such zeolites can range from about 100 mgs to as high as about 3.0 g, and such doses can be repeated as often as appropriate.

An alternative preferred zeolite composition can be prepared by treating an existing zeolite material with suitable alternative salt solutions to improve the cation exchange ability and/or selectivity. For example, the IE-W-85 as well as several other commercially available zeolites are produced with high levels of potassium. As such, when it is desired to reduce the level of potassium contained in the zeolite, and ultimately improve the zeolite selectivity as well as reduce the dose of potassium received in combination with said zeolite, one may treat the zeolite with an appropriate amount of sodium chloride or calcium chloride. By treating the potassium-containing zeolite in this fashion, the sodium and/or calcium ions at least partially replace the potassium ions contained in the commercially available product. In this manner, the sodium, potassium and calcium levels in the zeolite can be adjusted as desired. The zeolite used in the present invention can be given in doses which range from about 100 mgs to as high as about 3.0 g, and such doses can be repeated as appropriate.

It should be noted that by incorporating the appropriate cation into the ion exchange zeolite it would be possible not only to remove the ammonium ions but also precipitate the bicarbonate ions which also protect the *H. pylori* organism. This can be accomplished by including a cation which, when displaced from the ion exchange material, will react with the bicarbonate to form an insoluble compound. Thus, for example, when calcium ions are displaced from the zeolite, they will be able to react with the bicarbonate to form the highly insoluble calcium carbonate.

The compounds are orally administered as described above in amounts which are effective for treating a mammal for the presence or activity of *H. pylori* in the gastrointestinal tract in the presence of bicarbonate or ammonium ions or in the presence of urea, which are scavenged, reacted with or inactivated by the therapeutic compounds referred to above, to remove said bicarbonate or ammonium ions or urea from the basic protective layer which surrounds such *H. pylori* thus permitting the acid environment to react with the microorganisms and prevent further growth or activity. As such, it is contemplated that the compounds referred to above are useful for the treatment of gastritis, and gastric or duodenal ulcer disease.

Alternative embodiments of the invention described herein combine the compounds referred to above. The appropriate doses of each of these compounds may be reduced to account for additive or synergistic increases in activity when the compounds are used in combination.

Additionally, the compounds referred to above may be used or administered in combination with a mucoadhesive. The mucoadhesive is useful for forming a gastrointestinal film, thus concentrating the compounds in the region of the gastric mucosa where the compounds are most effective. Representative examples of mucoadhesives which can be used in combination with the active compounds noted above may be selected from sucralfate, polycarbophil, hydroxyethylmethacrylate, polyacrylic acid, carboxymethylcellulose, hydroxypropylcellulose, polyethylene glycol, polyalkylcyanoacrylate as well as other such mucoadhesives.

Numerous pharmaceutical compositions are contemplated as falling within the scope of the invention described herein. The active compounds may be administered in the form of a pharmaceutical composition which contains effective doses of one or more of the compounds noted above alone or in combination with a pharmaceutically acceptable carrier. Representative examples of orally administered dosage forms include tablets which may be swallowed whole or chewed, capsules which are rapidly dissolvable, such that the active ingredient is released in the stomach, solutions which contain effective amounts of the ingredients noted above, suspensions, slurries, powders, gels and the like.

Additionally, the active compounds may be administered in combination with microcapsules. Each such microcapsule is preferably comprised of a substantially water-insoluble wall, but which is relatively permeable to urea, ammonia, water and other small molecules, e.g., ions, but substantially impermeable to proteins, polypeptides, dialdehyde polysaccharides and other large molecules as well as particulate matter. A plurality of such microcapsules can be used in tablet or capsule formulating. These microcapsules can also be used in combinations which include the mucoadhesives, pharmaceutically acceptable adjuvants and the like.

The ammonia, bicarbonate and urea scavenging or reactive compounds noted above may also be used for the treatment or prevention of dermatitis or skin rash. The compounds are used alone or in combination by applying to the skin or by applying to a substrate in which the skin is wrapped. In particular, the compounds are effective for preventing or treating diaper rash.

As used herein, the term "diaper rash" is not limited to occurrences seen in infants. Rather, this term encompasses both diaper dermatitis in children and dermatitis in incontinent adults. A feature which is shared by both children and adults is the site of involvement, i.e., the area usually covered by the diaper. A complete description of the clinical symptoms of diaper rash may be found in *Pediatrics* (Seventeenth Edition) at page 855 and in *Pediatrics Dermatology* (Vol. 1) at page 708-710 (1988).

The preferred compounds for use in the prevention or treatment of diaper rash include dibasic magnesium phosphate, dialdehyde polysaccharides and zeolite. These compounds may be used alone, in combination with each other or with the calcium compounds, calcium acetate, calcium chloride, calcium gluconate and calcium lactate as well as the magnesium compounds, magnesium chloride and magnesium citrate in amounts which are affective for treating, ameliorating or preventing diaper rash.

When applied to the skin, these compounds are typically used in the form of a topical composition. Effective amounts are applied to the skin to prevent or ameliorate the dermatitis. When applied topically, the compounds may be used in the form of pharmaceutically acceptable solutions, suspensions, slurries, gels, powders, patches, bandages, ointments, aerosols and creams.

Alternatively, the compounds may be incorporated into a substrate such as a diaper, where the compounds are believed to react with, complex, deactivate or otherwise prevent increases in the pH when it is combined with a urine/fecal mixture. Otherwise, the enzymes (e.g., protease, lipase) present in the feces may in turn be activated or enhanced.

Without limiting the invention to a specific mechanism, the compounds are believed to act in this regard by reacting with or deactivating the ammonium ions or urea present in the urine, which is believed to function in combination with the fecal bacteria and enzymes to cause dermatitis. The various bacterial enzymes (e.g., protease, lipase) have substantially increased activity at basic pH.

By applying the compounds to the skin, the ammonium ions and urea from urine are deactivated, and the added compounds tie up the bicarbonate. Similarly, by incorporating the compounds into a diaper, the compounds can react with and deactivate the urea or the ammonium ions present in the urine, as well as the bicarbonate, thus ultimately reducing the incidence or severity of the dermatitis.

Another alternative embodiment of the invention described herein relates to the use of the compounds described above for the treatment or prevention of diaper rash in combination with a coating of an adhesive, film-forming or barrier compound. Such combinations have improved film forming properties, which most preferably include permeability to gas and water vapor, but essentially impermeability to larger molecules such as enzymes and particulate material. In this fashion, the composition when applied to the skin adheres without substantially preventing water evaporation or otherwise clogging the pores, while keeping the fecal bacterial enzymes and particulate matter away from the skin, and further acting as a physical barrier for the skin, thus preventing skin irritation and the dermatitis which results from such contact.

Yet another alternative embodiment of the invention is a topical composition which is used to form a barrier against bacteria, bacterial components, such as enzymes, and particulate matter which may be irritating to the skin. The barrier is preferably permeable to gases and water to avoid unnecessarily irritating the skin, and is comprised of the coating compounds noted above without the urea and/or ammonia and/or bicarbonate ion deactivating components present. This composition typically contains a film-forming effective amount of at least one member selected from the group consisting of polycarbophil, hydroxyethyl methacrylate, polyacrylic acid, carboxymethylcellulose, hydroxypropylcellulose, polyethylene glycol and polyalkylcyanoacrylate. These compounds can be applied topically to the skin at an effective concentration, to form a film-type barrier to large molecules. Thus, these compounds can act as topical barriers, without the scavenging/reacting compounds noted above.

Another embodiment of the invention encompasses one or more of the compounds noted above in combination with a substrate in the form of a treated (or rash-reducing) diaper. In this aspect of the invention, the diaper substrate is treated with an effective amount of one or more of the scavenging/inactivating compounds noted above. Representative amounts range from about 10 mls of a 1% (w/v) aqueous suspension of dibasic magnesium phosphate to as high as necessary to reduce the incidence or severity of dermatitis when diapers treated in this manner are used with regularity.

Another alternative embodiment of the invention utilizes a diaper, which may be comprised of, e.g., paper and cloth or some other substrate, in combination with a dialdehyde polysaccharide. The dialdehyde polysaccharide may optionally be in the form of a matrix which is effective for absorbing ammonium ions and reacting with urea. This matrix may also be combined with dibasic magnesium phosphate, dialdehyde starch in non-matrix form and/or zeolite as described above. Similarly, the dialdehyde polysaccaride in matrix form may be used singularly or in combination with the other ingredients in the form of a barrier or ointment which is applied to the skin topically prior to application of the diaper.

When applied to the skin prior to wrapping the skin in a diaper, the compounds noted above may be used in combination with numerous pharmaceutically acceptable carriers such as petrolatum, PEG, other creams and ointment bases, talcum powder, corn starch, etc. The active compound is typically present in an amount which is effective for preventing or minimizing the incidence of diaper rash. This can range from about 0.01% (w/w) by weight to essentially 100% (w/w). For example, a zeolite can be used in the form of a dusting powder with or without talc or another pharmaceutically acceptable carrier therefore.

When incorporated into the cloth or paper of the diaper prior to use, essentially the same dosages can be applied to this substrate. For example, a suspension of dibasic magnesium phosphate can be used to treat the diaper ranging from about 0.1% to 20% (w/v) or higher depending upon the needs of the particular individual for which the diaper was prepared, the type of material used to make the diaper and other factors.

Certain preferred embodiments of the invention are described below in the examples. However the scope of the claims is not to be limited thereby.

EXAMPLE 1

EFFECTIVENESS OF COMPOUNDS ON *H. PYLORI*

Compounds were tested as described below for activity as a function of pH, based on a modification of the test procedure set forth in *J. Clin. Pathol.* Vol. 40, p. 1387 (1987) incorporated herein by reference.

The specific test procedures were utilized in the experiment.

1. Bacteria were suspended in 100 mM citrate phosphate buffer at pH 8.5 to give about $10^9$ organisms/ml
2. 50 ul of this suspension was inoculated into the following:
    a) 1 ml of 100 mM citrate phosphate buffer at a pH of 2.5, 3.5 and 4.5 without 6 mM urea;
    b) same as 2a) with 6 mM urea;
    c) same as 2b) but with the test compounds added.
3. The mixtures prepared in accordance to step #2 above are placed in wells of 24-well tissue culture plates which are maintained in BBL Campy pouches at 37° C. for 60 minutes, while agitated in a control environment incubator/shaker.
4. After 60 minutes of incubation, the suspensions were subcultured onto blood agar plates using a 10 ul loop. The plates were incubated microaerophilically at 37° C. for 72 hours and then scored.

The test compounds used in this experiment are set forth below:

| | COMPOUNDS |
|---|---|
| A: | dibasic magnesium phosphate |
| B: | dialdehyde starch |
| C: | calcium acetate |
| D: | calcium chloride, anhydrous |
| E: | d-glucuronic acid, hemicalcium salt |
| F: | L(+)lactic acid, hemicalcium salt, hydrate |
| G: | magnesium chloride, anhydrous |
| H: | citric acid, magnesium salt, dibasic, hydrate |
| I: | zeolite (UOP Molecular Sieve Type IE-W-85) Na/K form |
| Ia: | zeolite I treated with 1M NaCl solution |
| Ib: | zeolite I treated with 1M CaCl$_2$ solution |

The *H. pylori* growth indices were scored on the following basis:

| 0: | no colonies in streak |
|---|---|
| <1: | few isolated colonies |
| 1: | <30 colonies at the top of streak |
| 2: | >30 individual colonies at top of streak. No colonies at bottom of streak. |
| 3: | Non-confluent growth at top of streak; little or no growth at bottom. |
| 4: | Confluent growth at top of streak, with growth to single colonies down full streak. |

The doses of the compounds used in these examples are approximately twenty times the theoretical stoichiometric requirement. The dosing levels used are set forth below.

| COMPOUND | DOSING INFORMATION |
|---|---|
| A | 42 g/l |
| B | 42 g/l |
| C | 20 g/l |
| D | 14 g/l |
| E | 52 g/l |
| F | 32 g/l |
| G | 12 g/l |
| H | 30 g/l |
| I, Ia, Ib | 42 g/l |

The effect of the test compounds on the growth of H. pylori in the presence of 6 mM urea, after it has been cultured in pH buffers of 2.5, 3.5 and 4.5 was measured. The results are shown below in Table I.

TABLE I

| Effect of test compounds on *H. pylori* growth at varied pH | | | |
|---|---|---|---|
| Compound(s) | pH = 2.5 | pH = 3.5 | pH = 4.5 |
| C | 0 | 1.3 | 2.5 |
| D | 0.5 | 1 | 1.5 |
| E | 1.2 | 2.5 | 2.7 |
| F | 0.5 | 0.5 | 0.75 |
| G | 2 | 2.5 | 3.3 |
| H | 2 | 2.5 | 3 |
| A | 1 | 2.3 | 3.3 |
| A + C | 0 | 1.7 | 2.3 |
| A + D | 0 | 1 | 1.7 |
| A + E | 0.3 | 1 | 2 |
| A + H | 0.67 | 1.3 | 2 |
| B | 0 | 0.7 | 0.5 |
| B + C | 0 | 0 | 0.75 |
| B + D | 0 | 0.3 | 0.3 |
| B + F | 0 | 0.3 | 0.25 |
| B + G | 0.75 | 0.75 | 1 |
| B + H | 0 | 0.5 | 0.9 |
| I | 1 | 2.3 | 2.7 |
| I + C | 0.3 | 2.7 | 2.3 |
| I + D | 0 | 1.7 | 2 |
| I + E | 0.67 | 2.7 | 2 |
| I + H | 0.77 | 3.3 | 2 |
| Ia | 2.8 | 1.8 | 2.1 |
| Ia + C | 1.5 | 2.1 | 2.8 |
| Ia + D | 1.3 | 1.4 | 1.8 |
| Ia + E | 1.9 | 1.8 | 2.3 |
| Ia + H | 3.3 | 2.8 | 2.3 |
| Ib | 2 | 2.3 | 2.7 |
| Ib + C | 0 | 1.7 | 2.7 |
| Ib + D | 1 | 1.7 | 2 |
| Ib + E | 0.67 | 2.3 | 1.7 |
| Ib + H | 1.5 | 3 | 3 |

Test materials included nutrient broth, *H. pylori* and 6 mM urea. Results noted above are the average of growth indices.

The average values for the positive (with urea) and negative (without urea) controls from the growth of *H. pylori* are indicated in Table II below.

TABLE II

| H. PYLORI CONTROL VALUES | | | |
|---|---|---|---|
| | pH = 2.5 | pH = 3.5 | pH = 4.5 |
| Growth without urea | 0.25 | 0.2 | 3.5 |
| Growth with urea | 2.5 | 3.5 | 2.4 |

The control value indicates that at low pH, the acid environment deactivates the *H. pylori*. However, when urea is present, the microorganisms are protected. At a pH of 4.5, urea protection no longer seems to be required. The data summarized in Table I indicates that the test compounds reduce or eliminate the growth of *H. pylori*. The *H. pylori* activity is further reduced when an ammonia and a bicarbonate scavenger are used together.

In general, the results appear to be most pronounced when urea protection is required, i.e., at low pH values. As the pH increases, the results are less compelling, as might be expected from the control results described above.

EXAMPLE 2

Purpose:

To determine the irritation inhibiting properties of selected compounds relative to a positive control on the skin.

Test Compounds:

Test compounds A, B, C, E, G and H described in Example 1 were utilized.

Test Animals:

New Zealand Albino rabbits, males and females, 2-3 Kg, Three (3) groups of eight (8) animals were used for four (4) treatments to each group (24 animals total).

Collection and Storage of Urine and Feces:

A urine and fecal sample was collected from a normal, health adult, and stored at $-20°$ C. in plastic screw-cap containers until use.

Storage of Test Article:

The test articles were stored in refrigerated conditions (4° C.).

Preparation of Test Materials:

Twelve test materials were prepared as follows;

Test Material Number 1 (Control):

A mixture of feces and urine (in a ratio of 5:1, weight of feces to volume of urine). The feces and urine were brought to ambient temperature and thoroughly mixed with a spatular, one (1) hour before use in the experiment. Prior to its use, the pH was checked to assure that it was at least 7.8. Excess material was discarded and new test material was prepared for later testing.

Test material Number 2:

Prepared as in (1), except that a 50% weight/volume amount of Compound A (0.2 grams), based on the volume of urine, was added to the test material.

Test material Number 3:

Same as (2), expect that a 50% weight/volume amount of Compound B (0.2 grams) was substituted for Compound A.

Test material Number 4:

Same as (2), except that a 25% weight/volume amount of Compound A and 11% weight/volume of Compound C were added.

Test material Number 5:

Same as (2), except that a 25% weight/volume amount of Compound A and 29% weight/volume of Compound E were added.

Test material Number 6:

Same as (2), except that a 25% weight/volume amount of Compound A and 17% weight/volume of Compound H were added.

Test material Number 7:

Same as (2), except that a 11% weight/volume amount of Compound E was added.

Test Material Number 9:

Same as (2), except that a 17% weight/volume amount of Compound H was added.

Test Material Number 10:

Same as (3), except that a 25% weight/volume amount of Compound B and 10% weight/volume amount of Compound G were added.

Test Material Number 11:

Same as (3), except that a 10% weight/volume amount of Compound G was added.

Test Material Number 12:

Same as (2), except that a 10% weight/volume amount of Compound G was added.

Procedure:

Patching sites were demarcated with a marking pen on the clipped skin of each animal. Each test material was applied to a 1 inch by 1 inch square, 2 ply gauze patch until saturated (approximately 0.5 grams). Each patch was applied to the appropriate test site and held in place with a one inch Elastoplast. Each animal was overwrapped with an orthopedic stockingette which was held in place by masking tape.

After being exposed for 24 hours, the patches were removed and new patches (with another application of the same material) were applied.

Twenty-four (24) hours after the second application, the patches were removed and the application sites were graded for erythema, edema and eschar. Grading was also performed at 48 and 72 hours after the second application. The scoring criteria employed were as follows:

Erythema
0=none
1=very slight
2=well defined
3=moderate to severe
4=severe (beet redness)

Edema
0=none
1=very slight
2=slight (edge of area well defined by definite raising)
3=moderate (raised approximately 1 mm)
4=severe (raised more than 1 mm and extending beyond area of exposure)

Eschar
0=none
1=slight
2=moderate
3=severe

Total possible score per animal=11. The results are shown below in Table III.

The result are shown below in Table III.

TABLE III

| Sample | 24* Hour Irritation Score | 24 Hour T/C Index | 72* Hour Irritation Score | 72 Hour T/C Index | Final Average Irritation Score | Final T/C Index |
|---|---|---|---|---|---|---|
| Material #1 Control | 3.6 | — | 1.1 | — | 2.4 | — |
| Test Material #2 | 2.9 | 0.81 | 1.4 | 1.27 | 2.2 | 0.92 |
| Test Material #3 | 2.6 | 0.72 | 0.9 | 0.82 | 1.8 | 0.75 |
| Test Material #4 | 3.1 | 0.86 | 1.4 | 1.27 | 2.3 | 0.96 |
| Test Material #5 | 2.9 | 0.81 | 0.6 | 0.55 | 1.8 | 0.75 |
| Test Material #6 | 3.6 | 1.00 | 1.1 | 1.00 | 2.4 | 1.00 |
| Test Material #7 | 2.1 | 0.58 | 0.5 | 0.45 | 1.3 | 0.54 |
| Test Material #9 | 2.5 | 0.69 | 0.8 | 0.73 | 1.7 | 0.71 |
| Test Material #10 | 2.9 | 0.81 | 0.9 | 0.82 | 1.9 | 0.79 |
| Test Material #11 | 1.6 | 0.44 | 0.5 | 0.45 | 1.1 | 0.46 |
| Test Material #12 | 3.3 | 0.92 | 1.9 | 1.73 | 2.6 | 1.08 |

*after initiation of the second application of test material.
T/C = Test Initiation Score/Control Irritation

EXAMPLE 3

Purpose:
To determine the irritation inhibiting properties of several additional test compounds relative to a control on the skin.

Test Compounds:
Test compounds A, B, C, E, G, H and I described in Example 1 were utilized.

Test Animals:
New Zealand Albino rabbits as described in Example 2.

Collection and Storage of Urine and Feces:
As described in Example 2.

Storage of Test Article:
The Test articles were stored in refrigerated conditions (4° C.).

Preparation of Test Materials:
Test Material Number 1 ("TM #1") (Control):
A mixture of feces and urine (in a ratio of 5:1, weight of feces to volume of urine) prepared as described in Example 2.

Test Material Number 2 ("TM #2"):
Prepared as in TM #1, except that a 50% w/v amount of Compound B and an 11% w/v amount of Compound C were added.

Test Material Number 3 ("TM #3"):
Same as TM #2, except that a 29% w/v amount of Compound E was substituted for 11% w/v amount of Compound C.

Test Material Number 4 ("TM #4"):
Same as TM #2, except that a 17% w/v amount of Compound H was substituted for the 11% w/v amount of Compound C.

Test Material Number 6 ("TM #6"):
Same as TM #1 except that a 75% w/v amount of Compound I was added.

Test Material Number 7 ("TM #7"):
Same as TM #6, except that a 10% w/v amount of Compound G was added.

Test Material Number 8 ("TM #8"):
Same as TM #2 except that a 50% w/v amount of Compound A and a 29% w/v amount of Compound E was substituted for Compounds B and C.

Procedure:
Patch sites were demarcated and test materials applied as described in Example 2.

Twenty-four (24) hours after the first application was initiated, the patches were removed and new gauze patches containing the same that materials were re-applied to the same sites.

Twenty-four (24) hours after the second application the patches were removed and the sites were graded for erythema, edema, and eschar. Grading was again performed at 24, 48 and 72 hours after the second application. The scoring criteria employed were as noted previously. The results are shown below in Table IV.

TABLE IV

| Sample | 24* hour Irrit. Score | 24 hour T/C Index | 48* hour Irrit. Score | 48 hour T/C Index | 72* hour Irrit. Score | 72 hour T/C Index | Final Average Irrit. Score | Final T/C Index |
| --- | --- | --- | --- | --- | --- | --- | --- | --- |
| Test Material #1 Control | 3.9 | — | 2.0 | — | 1.0 | — | 2.3 | — |
| Test Material #2 | 2.8 | 0.72 | 1.5 | 0.75 | 0.63 | 0.63 | 1.7 | 0.74 |
| Test Material #3 | 3.4 | 0.87 | 1.4 | 0.70 | 0.75 | 0.75 | 1.8 | 0.78 |
| Test Material #4 | 2.6 | 0.67 | 1.1 | 0.55 | 0.75 | 0.75 | 1.5 | 0.65 |
| Test Material #6 | 3.0 | 0.77 | 1.5 | 0.75 | 1.0 | 1.0 | 1.8 | 0.78 |
| Test Material #7 | 3.3 | 0.85 | 2.5 | 1.25 | 1.8 | 1.8 | 2.5 | 1.09 |
| Test Material #8 | 2.4 | 0.62 | 1.5 | 0.75 | 0.9 | 0.9 | 1.6 | 0.7 |

*after initiation of the second application of test material
T/C = Test Irritation Score/Control Irritation Score As will be noted from Examples 2 and 3, the irritation indices declined when the test compounds were used as compared to the controls. Since rabbit tests are commonly used for human topical irritation studies, this is a satisfactory model for diaper dermatitis.

While certain preferred embodiments of the invention have been described herein in detail, numerous embodiments will be apparent to those of ordinary skill in the art. Consequently, the scope of the claims appended hereto is not to be limited to the preferred embodiments herein.

What is claimed is:

1. A method of treating a mammal to inhibit the presence or activity of *H. pylori* in the gastrointestinal tract comprising inactivating the *H. pylori* protective environment by orally administering to said mammal an effective amount of a scavenging, reacting or inactivating compound to remove the bicarbonate ions, ammonium ions or urea which afford the *H. pylori* protective environment, thereby exposing the *H. pylori* to deactivation by the acid environment of the gastrointestinal tract.

2. A method according to claim 1, wherein the compound is a chemical salt which reacts with the bicarbonate ions to form an insoluble bicarbonate compound.

3. A method according to claim 2 wherein the chemical salt is a magnesium or calcium compound which reacts with bicarbonate ions to form a water-insoluble calcium or magnesium bicarbonate compound.

4. A method according to claim 1 wherein the compound is an ion exchange material which inactivates ammonium or bicarbonate ions.

5. A method according to claim 1 wherein the compound is selected from the group consisting of a dibasic magnesium phosphate, dialdehyde polysaccharide, calcium acetate, calcium chloride, calcium gluconate, calcium lactate, magnesium chloride, magnesium citrate and zeolite.

6. A method according to claim 5 wherein the compound is a dialdehyde polysaccharide.

7. The method according to claim 5 wherein the zeolite administered is a mixed sodium/potassium zeolite which has ammonium ion selectivity.

8. The method according to claim 7 wherein the zeolite is pretreated with a sodium chloride solution in an amount effective for exchanging potassium ions contained therein for sodium ions.

9. The method according to claim 7 wherein the zeolite is pretreated with a calcium chloride solution in an amount effective for exchanging potassium and sodium ions for calcium ions.

10. The method according to claim 5 wherein the dibasic magnesium phosphate administered is represented by the formula, exclusive of water of hydration,

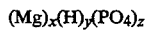

$$(Mg)_x(H)_y(PO_4)_z$$

wherein the Mg to $PO_4$ ratio (x/z) is in the range of 1.04 to 1.3, and y is in the range of about 0.4 and 1.

11. The method according to claim 10 wherein the Mg to $PO_4$ ratio (x/z) is about 1.1.

12. The method according to claim 5 wherein the compound is administered in combination with a mucoadhesive.

13. A method according to claim 12 wherein the mucoadhesive is selected from the group consisting of sucralfate, polycarbophil, hydroxyethyl methacrylate, polyacrylic acid, carboxymethylcellulose, hydroxypropylcellulose, polyethylene glycol and polyalkyl cyanoacrylate.

14. A method according to claim 5 wherein one or more of the selected compounds is contained within microcapsules, each such microcapsule having a water-insoluble wall permeable to urea, ammonia, water and other small molecules and ions, but impermeable to proteins, polypeptides, dialdehyde polysaccharide, other large molecules and particulate matter.

15. A method of treating a patient for gastrointestinal disease in which H. pylori is suspected as an etiologic agent comprising inactivating the H. pylori protective environment by orally administering to said patient an effective amount of a compound selected from the group consisting of dibasic magnesium phosphate, dialdehyde polysaccharide, calcium acetate, calcium chloride, calcium gluconate, calcium lactate, magnesium chloride, magnesium citrate and zeolite, sufficient to remove the bicarbonate ions, ammonium ions or urea which result in the H. pylori protective environment, thereby exposing the H. pylori to deactivation by the acid environment of the gastrointestinal tract.

16. A method according to claim 15 wherein the gastrointestinal disease is gastric or duodenal ulcer disease.

17. A method according to claim 15 wherein the gastrointestinal disease is gastritis.

18. The method according to claim 15 wherein the compound is administered in combination with a mucoadhesive.

19. A method according to claim 18 wherein the mucoadhesive is selected from the group consisting of sucralfate, polycarbophil, hydroxyethyl methacrylate, polyacrylic acid, carboxymethylcellulose, hydroxypropylcellulose, polyethylene glycol and polyalkyl cyanoacrylate.

20. A method according to claim 15 wherein one or more of the selected compounds is contained within microcapsules, each such microcapsule having a water-insoluble wall permeable to urea, ammonia, water and other small molecules and ions, but impermeable to proteins, polypeptides, dialdehyde polysaccharide, other large molecules and particulate matter.

21. A method of treating or preventing skin rash in a mammal resulting from exposure to the urease, urea, ammonia and/or bicarbonate of urine and feces, comprising:

exposing the skin to a substantially non-irritating compound selected from the group consisting of dibasic magnesium phosphate, dialdehyde polysaccharide and zeolite, which scavenges, reacts with or deactivates the urea, ammonia or bicarbonate.

22. A method according to claim 21 wherein the skin is exposed to the compound by pre-application of said compound to a diaper in an amount effective to prevent or minimize the occurrence or severity of said rash, and wrapping the skin in said diaper.

23. A method according to claim 21 wherein said compound is used in combination with at least one compound selected from the group consisting of calcium acetate, calcium chloride, calcium gluconate, calcium lactate, magnesium chloride and magnesium citrate.

24. An oral pharmaceutical composition for the inhibition of H. pylori which consists essentially of at least one compound selected from the group consisting of dibasic magnesium phosphate and dialdehyde polysaccharide, in combination with at least one compound selected from the group consisting of calcium acetate, calcium chloride, calcium gluconate, calcium lactate, magnesium chloride and magnesium citrate;

said compounds being present in the composition in an amount effective for the inactivation of the H. pylori protective environment in the gastrointestinal tract of a patient in need of such treatment, and an oral pharmaceutically acceptable carrier therefor.

25. The pharmaceutical composition according to claim 24 in the form of a powder, solution, suspension, slurry, gel, tablet or capsule.

26. A topical composition for the treatment or prevention of skin rash resulting from exposure to the urease, urea, ammonia and/or bicarbonate of urine and feces which consists essentially of at least one compound selected from the group consisting of dibasic magnesium phosphate, dialdehyde polysaccharide and zeolite, and a compound selected from the group consisting of calcium acetate, calcium chloride, calcium gluconate, calcium lactate, magnesium chloride and magnesium citrate;

said compounds being present in the composition in an amount effective to deactivate the urea, ammonia and/or bicarbonate, and a topical carrier therefor.

27. A composition according to claim 26 in the form of a solution, suspension, slurry, gel, powder, patch, bandage, cloth, paper, ointment or cream.

28. A composition according to claim 26, further comprising a mucoadhesive compound which forms a film essentially impermeable to enzymes and particulate matter, but permeable to gases and water vapor.

29. A composition according to claim 28 wherein the film forming composition is a mucoadhesive material selected from the group consisting of polycarbophil, hydroxyethyl methacrylate, polyacrylic acid, carboxymethylcellulose, hydroxypropylcellulose, polyethylene glycol and polyalkylcyanoacrylate.

30. A composition according to claim 29 in the form of a solution, suspension, slurry, gel, powder, patch, bandage, cloth, paper, ointment or cream.

31. A composition according to claim 26, further comprising a mucoadhesive compound which forms a film which is permeable to gases and water vapor, but essentially impermeable to large molecules, such as enzymes and particulate matter.

32. A composition according to claim 31 wherein the film forming composition is a mucoadhesive material selected from the group consisting of polycarbophil, hydroxyethyl methacrylate, polyacrylic acid, carboxymethylcellulose, hydroxypropylcellulose, polyethylene glycol and polyalkylcyanoacrylate.

33. A diaper comprised of a substrate material in combination with a composition according to claim 26.

34. An oral pharmaceutical composition for the inhibition of *H. pylori* which consists essentially of a zeolite and at least one compound selected from the group consisting of calcium acetate, calcium chloride, calcium gluconate, calcium lactate, magnesium chloride and magnesium citrate;

said zeolite and said compound being present in the composition in an amount effective for the inactivation of the *H. pylori* protective environment in the gastrointestinal tract of a patient in need of such treatment, and administered in combination with a mucoadhesive, and an oral pharmaceutically acceptable carrier therefor.

35. An oral pharmaceutical composition for the inhibition of *H. pylori* which comprises a dialdehyde polysaccharide and at least one compound selected from the group consisting of calcium acetate, calcium chloride, calcium gluconate, calcium lactate, magnesium chloride and magnesium citrate, said dialdehyde polysaccharide and said compound being present in the composition in an amount effective for the inactivation of the *H. pylori* protective environment in the gastrointestinal tract of a patient in need of such treatment, and administered in combination with a mucoadhesive, and an oral pharmaceutically acceptable carrier therefor.

* * * * *